(12) United States Patent
Kato

(10) Patent No.: US 11,969,154 B2
(45) Date of Patent: Apr. 30, 2024

(54) IMAGING SYSTEM AND ENDOSCOPIC DEVICE

(71) Applicant: OLYMPUS CORPORATION, Hachioji (JP)

(72) Inventor: Shuichi Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 506 days.

(21) Appl. No.: 17/161,849

(22) Filed: Jan. 29, 2021

(65) Prior Publication Data

US 2021/0145250 A1 May 20, 2021

Related U.S. Application Data

(63) Continuation of application No. PCT/JP2018/029222, filed on Aug. 3, 2018.

(51) Int. Cl.
*A61B 1/00* (2006.01)
*A61B 1/045* (2006.01)

(52) U.S. Cl.
CPC .......... *A61B 1/045* (2013.01); *A61B 1/00006* (2013.01); *A61B 1/00009* (2013.01)

(58) Field of Classification Search
CPC .. A61B 1/045; A61B 1/00006; A61B 1/00009
USPC ........................................................ 600/109
See application file for complete search history.

(56) References Cited

U.S. PATENT DOCUMENTS

2010/0185055 A1* 7/2010 Robertson ............ A61B 5/0073
600/117
2012/0323073 A1* 12/2012 Azuma .............. A61B 1/00018
600/110

FOREIGN PATENT DOCUMENTS

| JP | 11-252438 A | 9/1999 |
|---|---|---|
| JP | 2002-185853 A | 6/2002 |
| JP | 2006-303582 A | 11/2006 |
| JP | 2007-110355 A | 4/2007 |
| JP | 2011-206333 A | 10/2011 |
| JP | 2013-466 A | 1/2013 |

(Continued)

OTHER PUBLICATIONS

Wikipedia, "Differential signaling", Nov. 28, 2015. https://web.archive.org/web/20151128155106/https://en.wikipedia.org/wiki/Differential_signaling.*

(Continued)

*Primary Examiner* — Timothy J Neal
*Assistant Examiner* — James Edward Boice
(74) *Attorney, Agent, or Firm* — WHDA, LLP

(57) ABSTRACT

An imaging system includes: a solid-state imaging device that transmits an imaging signal of a continuous image that has been captured; and a control device that processes the imaging signal transmitted from the solid-state imaging device, and to control an operation of the solid-state imaging device. The solid-state imaging device includes: a pixel unit that acquires the imaging signal; a register that stores a setting value that defines the operation of the solid-state imaging device; a processing circuit that converts the imaging signal into a digital imaging signal; a frame configuration circuit that generates a serial digital transmission signal that is acquired by embedding a synchronizing signal synchronized with a horizontal synchronizing signal of the captured image in the digital imaging signal as a first serial clock signal; and a data transmission unit that transmits data of the digital transmission signal.

7 Claims, 5 Drawing Sheets

(56) References Cited

FOREIGN PATENT DOCUMENTS

JP            5356632 B1    12/2013
JP      2017-176348 A    10/2017

OTHER PUBLICATIONS

Wikipedia, "Manchester code", Aug. 4, 2015. https://web.archive.org/web/20150804010321/https://en.wikipedia.org/wiki/Manchester_code.*

Iwane (JP2013000466A), English translation with examiner-added page numbers and line numbers.*

Shigehisa (JP2017176348A), English translation with examiner-added page numbers and line numbers.*

Tokitsune (JP2006303582A), English translation with examiner-added page numbers and line numbers.*

International Search Report dated Sep. 25, 2018, issued in counterpart International Application No. PCT/JP2018/029222 (3 pages, including Japanese original and English translation).

* cited by examiner

IMAGING SYSTEM AND ENDOSCOPIC DEVICE

CROSS REFERENCE TO RELATED APPLICATIONS

This application is a continuation application based on a PCT Patent Application No. PCT/JP2018/029222, filed on Aug. 3, 2018, the entire content of which is hereby incorporated by reference.

BACKGROUND

Technical Field

The present invention relates to an imaging system and an endoscopic device using the imaging system.

Background Art

Since the past, endoscopic devices which are inserted into the bodies of patients (subjects to be inspected) to image or treat their affected parts have been put into practical use. Incidentally, recently in the medical industry, with the aging of patients, minimally invasive medical treatment with a smaller burden (invasiveness) on the bodies of the patients has been promoted. The endoscopic devices are also required to have minimal invasiveness. In order to realize minimal invasiveness in an endoscopic device, it is necessary to reduce the diameter of the insertion portion to be inserted into the body of a patient, which is an important issue.

In an endoscopic device, an image of an affected part of the body of a patient is captured by a solid-state imaging device provided at the distal end of the insertion portion, and a signal of the image captured by the solid-state imaging device is transmitted to the main body through a signal line provided in the insertion portion. In endoscopic devices, a charge coupled device (CCD)-type image sensor has been used hitherto as a solid-state imaging device. Incidentally, as a general solid-state imaging device, a complementary metal-oxide semiconductor (CMOS)-type image sensor has also been used hitherto. However, the adoption of the CMOS-type image sensor as a solid-state imaging device in an endoscopic device has been postponed due to poor image quality. However, in recent years, techniques for the CMOS-type image sensor have improved, and its image quality that was a factor in the postponement of its adoption or the like has been enhanced. Recent CMOS-type image sensors have been adopted in many fields as a solid-state imaging device that replaces a CCD-type image sensor. Therefore, adopting a CMOS-type image sensor as a solid-state imaging device in an endoscopic device is also being considered. In an endoscopic device, effects such as a decrease in power consumption, the realization of multi-functionality, or a decrease in the diameter of the insertion portion are expected with the switch from the CCD-type image sensor to the CMOS-type image sensor.

More specifically, unlike the CCD-type image sensor, the CMOS-type image sensor can be driven by a power supply having a single voltage. Therefore, by adopting the CMOS-type image sensor as a solid-state imaging device in an endoscopic device, it is possible to reduce the number of power supply lines more than when a CCD-type image sensor requiring a power supply having a plurality of voltages is adopted, and to realize a decrease in the diameter of the insertion portion. In addition, by adopting the CMOS-type image sensor as a solid-state imaging device in an endoscopic device, it is possible to set the voltage of a power supply to be lower than when the CCD-type image sensor is adopted, and to realize low power consumption.

In addition, the CMOS-type image sensor can be configured such that the size of a pixel is made smaller than in the CCD-type image sensor due to a difference in the structure of pixels disposed in a pixel unit that receives light. Therefore, by adopting the CMOS-type image sensor as a solid-state imaging device in an endoscopic device, it is possible to realize a decrease in the size of the distal end of the insertion portion more easily than when the CCD-type image sensor is adopted.

In addition, the CCD-type image sensor needs to be manufactured using a dedicated manufacturing process, whereas the CMOS-type image sensor can be manufactured using the same manufacturing process as other integrated circuits such as a general LSI. Therefore, in the CMOS-type image sensor, it is possible to cope with a system on chip (SOC) easily, and to realize multi-functionality of a solid-state imaging device. Therefore, by adopting the CMOS-type image sensor as a solid-state imaging device in an endoscopic device, it is possible to realize multi-functionality easily.

For example, in a case where the CCD-type image sensor is adopted as a solid-state imaging device in an endoscopic device, an analog pixel signal which is output from the CCD-type image sensor is transmitted to the main body through a thin signal line provided in the elongated insertion portion, and thus it is necessary to secure the quality of an analog signal (a pixel signal) to be transmitted by driving the pixel signal with a large drive circuit. Consequently, in an endoscopic device having a CCD-type image sensor adopted as a solid-state imaging device, a configuration in which an analog pixel signal is converted into a digital pixel signal and is transmitted to the main body can be considered. However, in the case of such a configuration, although a large drive circuit is not required, peripheral circuits such as a driving signal generation circuit or an analog-digital (AD) conversion circuit need to be disposed at the distal end of the insertion portion as a separate chip from the CCD-type image sensor, which leads to an increase in the number of parts to be disposed at the distal end portion. On the other hand, in the CMOS-type image sensor, peripheral circuits including not only a driving signal generation circuit or an AD conversion circuit but also a processing circuit such as a correlated double sampling (CDS) circuit or an image processing circuit can be formed inside the CMOS-type image sensor. Further, in the CMOS-type image sensor, a technique of forming pixels and peripheral circuits on different semiconductor substrates and laminating the semiconductor substrates to constitute one CMOS-type image sensor is also established. Therefore, in the CMOS-type image sensor, even though peripheral circuits are formed inside, a case in which the size of the semiconductor substrate, that is, the chip area (projection area) of the CMOS-type image sensor, increases does not occur. For this reason, even in a case where the endoscopic device is configured such that a digital pixel signal is transmitted to the main body by adopting the CMOS-type image sensor as a solid-state imaging device, it is possible to reduce the number of parts to be disposed at the distal end portion more than when the CCD-type image sensor is adopted, and to realize a decrease in the size of the distal end of the insertion portion.

In an endoscopic device, as described above, it is possible to realize a decrease in the diameter of the insertion portion by utilizing advantages that the CMOS-type image sensor has over the CCD-type image sensor, such as that it can be driven by a power supply having a single voltage, has a small pixel, and can have peripheral circuits such as a driving signal generation circuit formed inside.

Incidentally, in a case where a multi-functional CMOS-type image sensor is adopted as a solid-state imaging device in an endoscopic device, the operation or execution of various functions including a function of image capturing provided in the CMOS-type image sensor is controlled from the main body. More specifically, the main body controls the operation or execution of each function by rewriting a setting value stored in a register that holds a setting corresponding to each function provided in the multi-functional CMOS-type image sensor. Therefore, the main body is provided with a mechanism for controlling rewriting of the register provided in the CMOS-type image sensor.

Here, a serial communication scheme can be used as a method of controlling rewriting of the register provided in the CMOS-type image sensor. Meanwhile, a serial communication scheme having the smallest number of control signals in a general technique of the related art is a 2-wire serial communication scheme. Examples of the 2-wire serial communication scheme include serial communication of an inter-integrated circuit (I2C) scheme and the like.

In other words, when the multi-functional CMOS-type image sensor is adopted as a solid-state imaging device in an endoscopic device, at least two signal lines are newly required for a control signal for controlling rewriting of the register even in the case of I2C serial communication. The size of the chip area (projection area) of the CMOS-type image sensor depends on the number of signal lines to be connected to an external circuit, that is, the number of pads to be formed on the semiconductor substrate of the CMOS-type image sensor as a reduction in the chip area proceeds. Therefore, in an endoscopic device, it is possible to realize a decrease in the diameter of the insertion portion, as described above, by adopting the CMOS-type image sensor as a solid-state imaging device. However, in order to realize a further decrease in the size of the insertion portion, it is required to further reduce the number of signal lines provided in the insertion portion connected to the CMOS-type image sensor.

For example, Japanese Unexamined Patent Application, First Publication No. H11-252438 (hereinafter referred to as Patent Document 1) and Japanese Unexamined Patent Application, First Publication No. 2007-110355 (hereinafter referred to as Patent Document 2) disclose techniques of reducing a portion of a control signal. In the technique disclosed in Patent Document 1, the number of signal lines is reduced by the camera main side multiplexing the control signal for controlling a camera head portion with a synchronizing signal to transmit the multiplexed signal and superimposing a clock signal on a power supply line to transmit the superimposed signal. In the technique disclosed in Patent Document 1, the clock signal is separated in the camera head portion, and the control signal multiplexed with the synchronizing signal is separated on the basis of the separated clock signal. Thereby, in the technique disclosed in Patent Document 1, the camera head portion performs an operation corresponding to control from the camera main side in accordance with the control signal. In addition, in the technique disclosed in Patent Document 2, the number of signal lines is reduced by superimposing carrier waves for modules to communicate with each other on a power line. In the technique disclosed in Patent Document 2, communication is performed between the modules by separating the carrier waves superimposed on the power line.

By applying the technique disclosed in Patent Document 1 or Patent Document 2 to reduce the control signal for controlling rewriting of the register provided in the CMOS-type image sensor, it is possible to reduce the number of signal lines provided in the insertion portion connected to the CMOS-type image sensor. More specifically, in a case where a configuration in which the register provided in the CMOS-type image sensor is rewritten using I2C serial communication is considered for an endoscopic device, it is possible to reduce one dedicated signal line for transmitting a serial clock signal SCL in I2C serial communication by superimposing the serial clock signal SCL supplied to the register through a dedicated signal line by the main body on the power supply line.

However, the techniques disclosed in Patent Document 1 and Patent Document 2 are configured such that a signal superimposed on the power supply line (power line) is separated on a side to be controlled. When this is applied to the CMOS-type image sensor in which the register is rewritten using I2C serial communication, the serial clock signal SCL superimposed on the power supply line is separated inside the CMOS-type image sensor, and the register is rewritten to a setting value indicated by a serial data signal SDA in I2C serial communication which is supplied from the main body through a dedicated signal line on the basis of the separated serial clock signal SCL. That is, it is necessary to provide a mechanism that separates the serial clock signal SCL superimposed on the power supply line inside the CMOS-type image sensor. The mechanism that separates the serial clock signal SCL provided in this register causes an increase in the circuit scale of the CMOS-type image sensor.

SUMMARY

The present invention provides an imaging system capable of reducing a portion of a signal in serial communication used in a solid-state imaging device and an endoscopic device using this imaging system.

An imaging system includes: a solid-state imaging device in which a plurality of pixels are arranged in a two-dimensional matrix, and configured to transmit an imaging signal of a continuous image that has been captured; and a control device configured to process the imaging signal transmitted from the solid-state imaging device, and to control an operation of the solid-state imaging device. The solid-state imaging device includes: a pixel unit configured to acquire the imaging signal; a register configured to store a setting value that defines the operation of the solid-state imaging device; a processing circuit configured to convert the imaging signal into a digital imaging signal by performing an analog/digital conversion; a frame configuration circuit configured to generate a serial digital transmission signal that is acquired by embedding a synchronizing signal synchronized with a horizontal synchronizing signal of the captured image in the digital imaging signal as a first serial clock signal; and a data transmission unit configured to transmit data of the digital transmission signal. The control device includes: a clock generation unit configured to generate a second serial clock signal synchronized with the first serial clock signal embedded in the digital imaging signal included in the digital transmission signal that has been transmitted; and a register setting unit configured to transmit a register setting signal that controls the register in synchronization with the second serial clock signal. The frame configuration circuit outputs the generated first serial clock signal to the register. The register determines a control represented by the transmitted register setting signal using the first serial clock signal output from the frame configuration circuit, and stores the setting value according to a determination result.

In the imaging system, the first serial clock signal may be a horizontal synchronizing signal corresponding to the image.

In the imaging system, a frequency of the first serial clock signal may be 1 kHz or more and 500 kHz or less.

In the imaging system, the data transmission unit may transmit data of the digital transmission signal by two differential signals, and the register setting unit may transmit the register setting signal by a single signal.

In the imaging system, the register setting unit may only transmit the register setting signal, not performing a reception of a signal.

In the imaging system, the solid-state imaging device may further include a clock oscillation circuit configured to oscillate and output a reference clock signal, the register setting unit may make the register store a setting signal of a oscillation frequency of the reference clock signal, and the clock oscillator circuit may oscillate the reference clock signal having a frequency according to the setting signal with the oscillation frequency stored in the register.

An endoscopic device includes the imaging system. The solid-state imaging device is arranged at a distal end of an insertion portion, and the control device is arranged in a main body.

According to each of the above aspects, it is possible to provide an imaging system capable of reducing a part of signals of serial communication used in a solid-state imaging device, and an endoscope device using this imaging system.

DETAILED DESCRIPTION OF THE PREFERRED EMBODIMENTS

Figure 1:
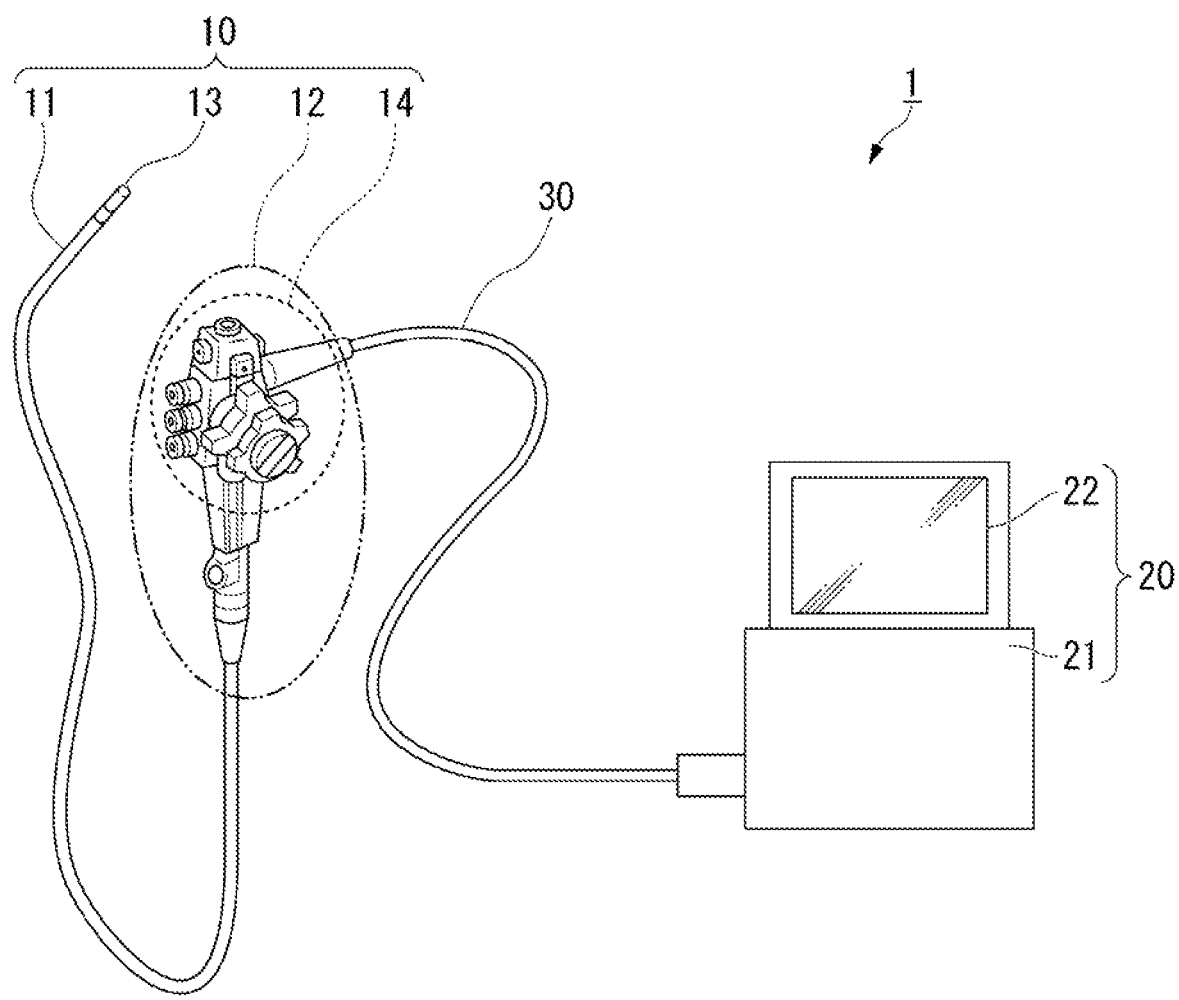
FIG. 1 is a configuration diagram illustrating a schematic configuration of an endoscopic device in an embodiment of the present invention.

Hereinafter, an embodiment of the present invention will be described with reference to the accompanying drawings. Meanwhile, a case in which an imaging system of the present invention is used as an endoscopic device of the present invention will be described below. FIG. 1 is a configuration diagram illustrating a schematic configuration of an endoscopic device in the embodiment of the present invention.

In FIG. 1, an endoscopic device 1 includes an endoscope portion 10 and a main body 20. The endoscopic device 1 is, for example, an endoscopic device for a digestive organ. The endoscopic device 1 is configured such that the insertion portion of the endoscope portion 10 is inserted into the body of a patient (a subject to be inspected) to capture an image of a region to be observed such as a lesion tissue in the digestive organ of the subject to be inspected. In this case, the endoscopic device 1 captures an image of the region to be observed using radiated light.

In the endoscopic device 1, the endoscope portion 10 includes an insertion portion 11 and an operation portion 12. In the endoscope portion 10, the insertion portion 11 is provided with an imaging portion 13 at its distal end. In addition, in the endoscopic device 1, the main body 20 includes an external processing portion 21 and a color monitor 22. In the endoscopic device 1, the operation portion 12 of the endoscope portion 10 and the external processing portion 21 of the main body 20 are connected to each other through a universal cord 30. Meanwhile, in the endoscopic device 1, the operation portion 12 of the endoscope portion 10 and a light source device (not shown) provided in the main body 20 are also connected to each other through a light guide (not shown) that transmits light with which a region to be observed is irradiated.

The endoscope portion 10 is configured such that the insertion portion 11 is inserted into the digestive organ or the like in the body of the subject to be inspected to capture an image of a region to be observed (hereinafter referred to as an "observation region"). In this case, the observation region is irradiated with illumination light guided by a light guide (not shown) from the distal end of the insertion portion 11. The endoscope portion 10 outputs (transmits) an imaging signal corresponding to the captured image of the observation region to the external processing portion 21 through a signal line in the universal cord 30.

The insertion portion 11 is inserted into the body of a subject to be inspected. The imaging portion 13 located at the distal end of the insertion portion 11 is provided with an image sensor that generates an imaging signal obtained by converting the image of the observation region into an electrical signal. The image sensor provided in the imaging portion 13 outputs (transmits) the generated imaging signal to the external processing portion 21 through the insertion portion 11, the operation portion 12, and the universal cord 30.

The operation portion 12 is a support portion for controlling operations of the insertion portion 11 and the imaging portion 13 by being operated by, for example, an inspection executor (such as, for example, a surgeon who is performing an operation on the digestive organs). In the endoscope portion 10, the operation portion 12 includes an operation switch 14 for controlling a direction when the distal end of the insertion portion 11 is inserted into the body of a patient or image capturing in the endoscopic device 1. The operation switch 14 outputs an instruction signal for giving an instruction for capturing an image of an observation region to the external processing portion 21 through the operation portion 12 and the universal cord 30 in accordance with, for example, an inspection executor's operation.

The external processing portion 21 is a control unit that controls the observation or imaging of an observation region which is performed by the image sensor provided in the imaging portion 13 of the endoscope portion 10. The external processing portion 21 transmits a control signal for the image sensor provided in the imaging portion 13 to control the observation or imaging of an observation region to the imaging portion 13 through signal lines in the universal cord 30, the operation portion 12, and the insertion portion 11. In addition, the external processing portion 21 is also an image processing device that performs predetermined image processing on an imaging signal of an observation region whose image is captured by the image sensor provided in the imaging portion 13 which is transmitted through the signal lines in the insertion portion 11, the operation portion 12, and the universal cord 30, and generates an image including the observation region whose image is captured. The external processing portion 21 is provided with a control unit that controls image capturing which is performed by the image sensor provided in the imaging portion 13 and generates an image on the basis of an imaging signal which is output from the image sensor.

In addition, the external processing portion 21 includes a light source device (not shown) that emits illumination light with which an observation region is irradiated in accordance with control from an inspection executor when the observation or imaging of the observation region is performed in the endoscopic device 1. The illumination light emitted by the light source device (not shown) is guided to the distal end of the insertion portion 11 of the endoscope portion 10 by, for example, light guides (not shown) or the like passing through the universal cord 30, the operation portion 12, and the insertion portion 11, and is radiated from the imaging portion 13 to observation region. Meanwhile, when the observation or imaging of an observation region is performed, the external processing portion 21 controls the light source device (not shown) and irradiates the observation region with the illumination light. The external processing portion 21 outputs an image signal of the generated image including the observation region to the color monitor 22 and displays it.

The color monitor 22 displays an image including the observation region corresponding to the image signal which is input from the external processing portion 21. The color monitor 22 is a display device such as, for example, a liquid crystal display (LCD).

With such a configuration, the endoscopic device 1 captures an image of an observation region such as a lesion tissue in the body of a patient (a subject to be inspected). The endoscopic device 1 presents an image including the observation region whose image is captured to an inspection executor.

Figure 2:
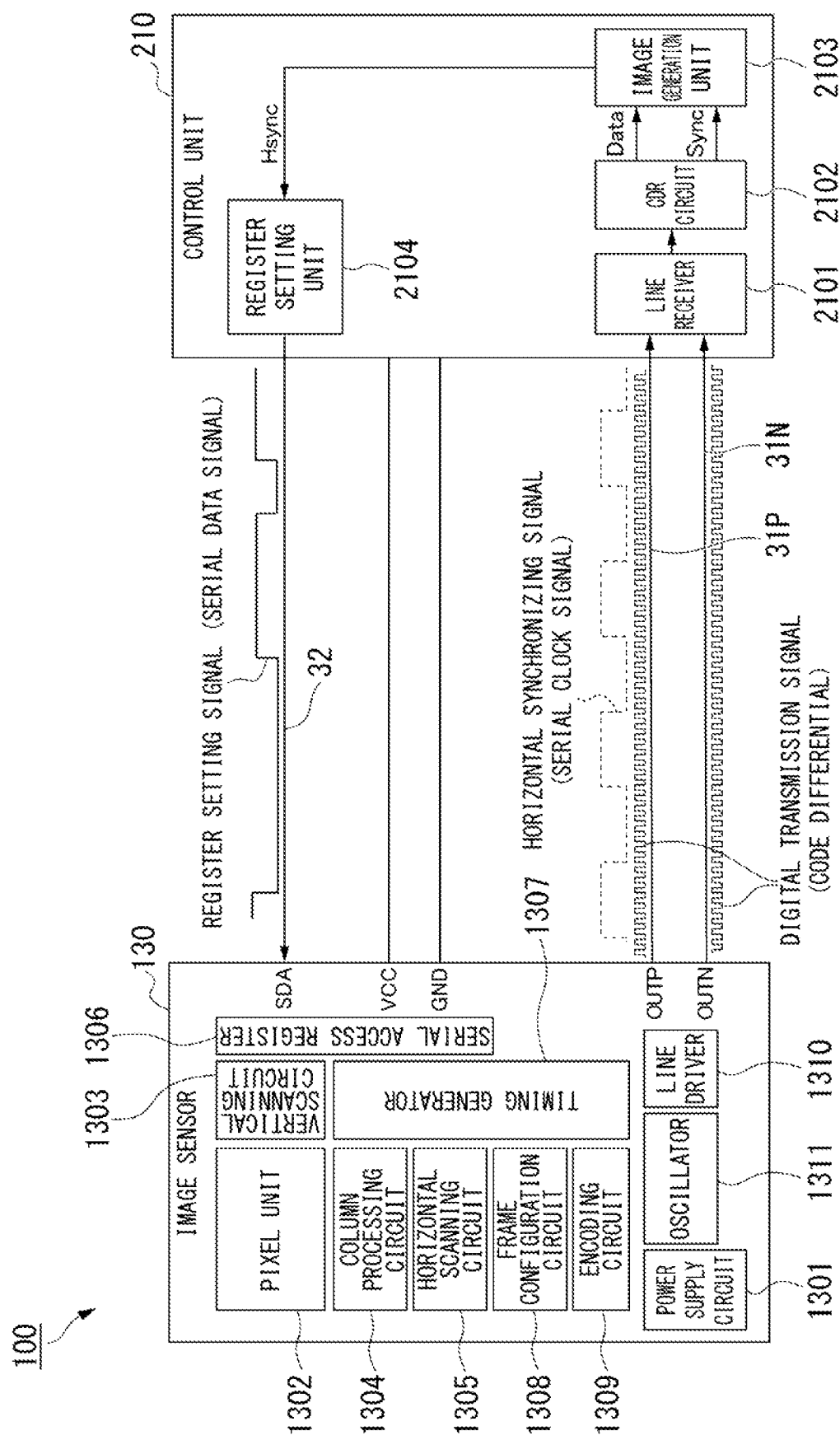
FIG. 2 is a block diagram illustrating a schematic configuration of an imaging system in the embodiment of the present invention.

Next, the configuration of an imaging system of the present invention will be described. In the endoscopic device 1, an imaging system is constituted by an image sensor provided in the imaging portion 13 configured in the insertion portion 11 and a control unit provided in the external processing portion 21 configured in the main body 20. FIG. 2 is a block diagram illustrating a schematic configuration of an imaging system in the embodiment of the present invention. In FIG. 2, an imaging system 100 is configured to include an image sensor 130 provided in the imaging portion 13 configured in the insertion portion 11 and a control unit 210 provided in the external processing portion 21 configured in the main body 20.

The image sensor 130 is a solid-state imaging device that exposes (detects) incident light in accordance with control from the control unit 210 and outputs an electrical signal obtained by photoelectrically converting the exposed light as an imaging signal. The image sensor 130 is a multi-functional complementary metal-oxide semiconductor (CMOS)-type image sensor. Meanwhile, the structure of the image sensor 130 is not particularly specified. Therefore, the image sensor 130 may be a structure in which all components are formed on one semiconductor substrate, or may be a structure in which a semiconductor substrate having pixels formed thereon and a semiconductor substrate having components other than the pixels formed thereon are laminated. The image sensor 130 captures a moving image in accordance with control from the control unit 210, and converts an imaging signal of the captured moving image into a digital imaging signal (hereinafter referred to as a "digital imaging signal") to transmit the converted signal to the control unit 210.

The control unit 210 is a control device that controls a function of image capturing in the image sensor 130, or the operation or execution of functions other than image capturing provided in the image sensor 130. In addition, the control unit 210 is also an image processing unit that generates an image obtained by performing predetermined image processing on the digital imaging signal of a moving image transmitted from the image sensor 130. The control unit 210 may be configured to include a processing device such as, for example, a central processing unit (CPU).

In the imaging system 100, in order to reduce the number of signal lines between the image sensor 130 and the control unit 210, a serial communication scheme in which data is controlled by a predetermined clock (hereinafter referred to as a "serial clock signal SCL") and a data signal synchronized therewith (hereinafter referred to as a "serial data signal SDA") is used for the transmission of a signal between the image sensor 130 and the control unit 210. Meanwhile, a serial communication scheme having the smallest number of control signals in the existing serial communication schemes is serial communication of an inter-integrated circuit (I2C) scheme in which data is controlled by two types of control signals. In serial communication of the present embodiment, data is controlled by the serial clock signal SCL and the serial data signal SDA according to the I2C. In addition, in the following description, the image sensor 130 is assumed to transmit a digital imaging signal to the control unit 210 using a serial transmission scheme of a low voltage differential signaling (LVDS) scheme which is a differential interface scheme.

In addition, in the imaging system 100, in order to further reduce the number of signal lines between the image sensor 130 and the control unit 210, the serial clock signal SCL in the I2C serial communication is reduced. Therefore, in the imaging system 100, the image sensor 130 embeds a clock signal equivalent to the serial clock signal SCL in the I2C serial communication in a digital imaging signal and transmits it to the control unit 210. In the imaging system 100, the control unit 210 transmits the serial data signal SDA in the I2C serial communication to the image sensor 130 in synchronization with a clock signal equivalent to the serial clock signal SCL embedded in a digital imaging signal and transmitted from the image sensor 130.

FIG. 2 shows a state in which the image sensor 130 embeds a horizontal synchronizing signal in a digital imaging signal as a clock signal equivalent to the serial clock signal SCL, that is, a differential signal of an LVDS scheme (a differential positive signal OUTP and a differential negative signal OUTN), and transmits it. In addition, FIG. 2 shows a state in which the control unit 210 transmits the serial data signal SDA to the image sensor 130 in synchronization with the transmitted horizontal synchronizing signal (the serial clock signal SCL) included in the differential signal of an LVDS scheme.

In this manner, in the imaging system 100, a serial signal line for transmitting the serial clock signal SCL out of two serial communication signal lines used for the control unit 210 to control the operation of the image sensor 130 is reduced, and only a serial signal line 32 for transmitting the serial data signal SDA is used. Meanwhile, in the imaging system 100, two signal lines of an LVDS scheme for the image sensor 130 to transmit a digital imaging signal to the control unit 210 are a differential signal line 31P for transmitting the differential positive signal OUTP and a differential signal line 31N for transmitting the differential negative signal OUTN. In FIG. 2, two power supply lines for supplying power from the control unit 210 to the image sensor 130, that is, a power supply line and a ground line are also shown together.

Thereby, in the endoscopic device 1 using the imaging system 100, signal lines in the endoscope portion 10 and the universal cord 30 can be reduced to only five signal lines of at least two power supply lines, that is, a power supply line and a ground line, two differential signal lines, that is, the differential signal line 31P and the differential signal line 31N, and the serial signal line 32. In this manner, in the endoscopic device 1 using the imaging system 100, it is possible to realize a decrease in the diameter of the endoscope portion 10 (particularly, the insertion portion 11).

Here, a more detailed configuration of components of the imaging system 100 will be described. First, the configuration of the image sensor 130 will be described. The image sensor 130 includes a power supply circuit 1301, a pixel unit 1302, a vertical scanning circuit 1303, a column processing circuit 1304, a horizontal scanning circuit 1305, a serial access register 1306, a timing generator 1307, a frame configuration circuit 1308, an encoding circuit 1309, a line driver 1310, and an oscillator 1311.

The power supply circuit 1301 generates a power supply of each voltage used in the image sensor 130 on the basis of power supplied from the control unit 210 through two power supply lines, that is, a power supply line and a ground line. The power supply circuit 1301 supplies the generated power to each component provided in the image sensor 130.

The oscillator 1311 is a clock oscillation circuit that generates a reference clock signal in the image sensor 130, that is, a so-called master clock signal on the basis of a setting value (parameter) stored in the serial access register 1306. The oscillator 1311 generates (oscillates) a master clock signal of a frequency based on the setting value (parameter) stored in the serial access register 1306. The oscillator 1311 supplies the generated master clock signal to each component provided in the image sensor 130.

Meanwhile, the oscillator 1311 is a component provided in the image sensor 130 in order to reduce the transmission of the master clock signal from the control unit 210 to the image sensor 130 in the imaging system 100, that is, the transmission line of the master clock signal between the image sensor 130 and the control unit 210. Therefore, in a case where the imaging system 100 is configured to transmit the master clock signal from the control unit 210 to the image sensor 130, the image sensor 130 can also be configured not to be provided with the oscillator 1311.

The pixel unit 1302 is a pixel array unit in which a plurality of pixels are disposed in a two-dimensional matrix. Each of the pixels disposed in the pixel unit 1302 generates signal charge of the amount of charge corresponding to the intensity of light incident on each disposed position, and stores the generated signal charge. Meanwhile, any one of an on-chip color filter that transmits light having a wavelength band of red (R), an on-chip color filter that transmits light having a wavelength band of green (G), and an on-chip color filter that transmits light having a wavelength band of blue (B) is attached to each of a plurality of pixels disposed in the pixel unit 1302 in the image sensor 130. Thereby, the image sensor 130 stores the generated color signal charge in accordance with the intensity of the incident light.

The vertical scanning circuit 1303 is a drive circuit that drives each pixel in the pixel unit 1302 for each row in accordance with control from the timing generator 1307 and outputs a voltage signal corresponding to the signal charge stored in each pixel as a pixel signal. Thereby, a pixel signal (analog signal) which is output by each pixel for each row is input to the column processing circuit 1304.

The column processing circuit 1304 is a processing circuit that performs predetermined analog signal processing on the analog pixel signal which is output from each pixel in the pixel unit 1302 by driving of the vertical scanning circuit 1303 in accordance with control from the timing generator 1307. More specifically, the column processing circuit 1304 performs a denoising process of removing noise included in the analog pixel signal through, for example, a correlated double sampling (CDS) process. In addition, the column processing circuit 1304 performs, for example, a signal amplification process of amplifying the signal level of the analog pixel signal or an analog/digital conversion (A/D conversion) process of converting the analog pixel signal into a digital value indicating the magnitude of the analog pixel signal with respect to the analog pixel signal on which the CDS process is performed. The column processing circuit 1304 sequentially outputs a digital imaging signal of a digital value indicating the magnitude of the analog/digital converted analog pixel signal to the frame configuration circuit 1308 in accordance with control from the horizontal scanning circuit 1305. Meanwhile, the digital imaging signal which is analog/digital converted by the column processing circuit 1304 is data of a parallel digital value.

Meanwhile, the column processing circuit 1304 may be configured to perform predetermined analog signal processing on an analog pixel signal for each column of the pixels disposed in the pixel unit 1302. That is, the column processing circuit 1304 may be configured to include one processing circuit that performs analog signal processing for each column of the pixels disposed in the pixel unit 1302. In addition, the column processing circuit 1304 may be configured to perform predetermined analog signal processing on the analog pixel signal for each a plurality of columns of the pixels disposed in the pixel unit 1302. That is, the column processing circuit 1304 may be configured to include one processing circuit that performs analog signal processing for each of a plurality of columns of the pixels disposed in the pixel unit 1302. In addition, the column processing circuit 1304 may be configured such that one processing circuit sequentially performs predetermined analog signal processing on the analog pixel signal which is output from the pixels of each column disposed in the pixel unit 1302.

The horizontal scanning circuit 1305 is a drive circuit that controls the column processing circuit 1304 for each column of each pixel in the pixel unit 1302 in accordance with control from the timing generator 1307 and sequentially outputs a digital imaging signal (digital value) which is analog/digital converted by the column processing circuit 1304 for each column of each pixel in the pixel unit 1302. Thereby, the digital imaging signal, analog/digital converted by the column processing circuit 1304, indicating the magnitude of the analog pixel signal which is output by each pixel is sequentially input to the frame configuration circuit 1308 for each column of each pixel disposed in the pixel unit 1302.

The frame configuration circuit 1308 is a processing circuit that configures each digital transmission signal for transmitting a moving image represented by each digital imaging signal sequentially output from the column processing circuit 1304 to the control unit 210 in accordance with control from the timing generator 1307. In this case, the frame configuration circuit 1308 adds information required for the control unit 210 having received digital imaging signals transmitted from the image sensor 130 to configure one frame (one image) of a corresponding moving image from a group of the received digital imaging signals.

More specifically, the frame configuration circuit 1308 generates synchronizing signals (a vertical synchronizing signal and a horizontal synchronizing signal) corresponding to each frame (image) constituting a moving image on the basis of the setting value (parameter) stored in the serial access register 1306. The frame configuration circuit 1308 configures a digital transmission signal for embedding information indicating the generated synchronizing signal in the digital imaging signal and transmitting it to the control unit 210. In other words, the frame configuration circuit 1308 configures a digital transmission signal for transmitting each frame (image) of a moving image in a state in which the generated synchronizing signal is embedded as a clock signal equivalent to the serial clock signal SCL used by the control unit 210. In this case, the frame configuration circuit 1308 may rearrange the digital imaging signals of each column sequentially output from the column processing circuit 1304, and configure a digital transmission signal in which the order of digital imaging signals (digital values) included in each frame (image) constituting a moving image is changed.

Meanwhile, information indicating a synchronizing signal included in the digital transmission signal of a moving image configured by the frame configuration circuit 1308 includes position information indicating the position of a row disposed in a frame (image) constituted of a group of the digital imaging signals. That is, in the information indicating a synchronizing signal, information indicating which row of digital imaging signals one row of digital imaging signals to be transmitted from now on corresponds to in a frame (image) of a moving image to be configured is included as information to be transmitted before the transmission of the digital imaging signal.

The frame configuration circuit 1308 sequentially outputs each piece of data included in the digital transmission signal of the configured moving image (information indicating a synchronizing signal such as position information or a digital imaging signal) to the encoding circuit 1309 for each row of a frame (image) of a moving image to be configured.

Thereby, the control unit 210 having received digital imaging signals transmitted from the image sensor 130 can determine which row of digital imaging signals each digital imaging signal corresponds to in one frame (image) of a moving image on the basis of the information indicating a synchronizing signal embedded in one frame (one image) of received digital imaging signals. In addition, the control unit 210 can detect at which timing a row is switched in a frame (image) of a moving image on the basis of the information indicating a synchronizing signal embedded in one frame (one image) of received digital imaging signals. That is, the control unit 210 can recognize the timing of synchronizing signals (a vertical synchronizing signal and a horizontal synchronizing signal) embedded by the frame configuration circuit 1308 in the digital imaging signal of each frame (image) of a moving image as a clock signal equivalent to the serial clock signal SCL from the information indicating a synchronizing signal for each row.

In addition, the frame configuration circuit 1308 outputs a horizontal synchronizing signal out of the generated synchronizing signals to the serial access register 1306 as the serial clock signal SCL used for serial communication in the image sensor 130.

Meanwhile, in the following description, a series of processing in the frame configuration circuit 1308 described above is referred to as a "frame configuration process."

The encoding circuit 1309 is an encoding circuit that converts (parallel/serial converts) each piece of data included in the digital transmission signal configured by the frame configuration circuit 1308 performing the frame configuration process in accordance with control from the timing generator 1307, that is, parallel data including information indicating a synchronizing signal such as position information or a digital imaging signal, into data indicated by one (single) serial signal, and further generates a digital transmission signal (code) which is an encoded single serial signal. As an encoding scheme when the encoding circuit 1309 encodes data indicated by a serial signal, various existing encoding schemes such as, for example, a Manchester encoding scheme or an 8b/10b encoding scheme can be considered.

The Manchester encoding scheme or the 8b/10b encoding scheme is an encoding scheme in which the control unit 210 having received a digital transmission signal (code) multiplexes a data detection clock for restoring each piece of data included in the digital transmission signal (code) (that is, information indicating a synchronizing signal such as position information indicated by a serial signal or a digital imaging signal) through clock data recovery. In encoding of the Manchester encoding scheme or the 8b/10b encoding scheme, data of each bit constituting a digital transmission signal of a single serial signal (hereinafter referred to as "bit data") is modulated so as to include a specific frequency component. Thereby, a synchronizing signal (data detection clock) synchronized with each piece of bit data of the digital transmission signal of a moving image configured by the frame configuration circuit 1308 is multiplexed in the digital transmission signal (code) of a single serial signal encoded by the encoding circuit 1309. This data detection clock is a clock signal in which a falling edge or a rising edge appears during a timing at which each piece of bit data obtained by serially converting each piece of parallel data included in the digital transmission signal of a moving image configured by the frame configuration circuit 1308 is switched. By detecting the bit data at the timing of this edge, it is possible to detect (restore) a logic of the bit data. Thereby, the control unit 210 can detect (restore) each piece of bit data from the received digital transmission signal (code) by extracting (restoring) the data detection clock through clock data recovery.

In the following description, the encoding circuit 1309 is assumed to encode each piece of data included in the digital transmission signal configured by the frame configuration circuit 1308 performing the frame configuration process using the Manchester encoding scheme. The encoding circuit 1309 sequentially outputs the digital transmission signal (code) of a single serial signal after Manchester encoding to the line driver 1310.

The line driver 1310 is a drive circuit that converts the digital transmission signal (code) which is a single serial signal output from the encoding circuit 1309 in accordance with control from the timing generator 1307 into digital transmission signals (code differentials) which are two serial differential signals, that is, the differential positive signal OUTP and the differential negative signal OUTN of an LVDS scheme and transmits it to the control unit 210. The line driver 1310 outputs a differential signal of each of the converted digital transmission signals (code differentials) from a corresponding output terminal.

The serial access register 1306 is a register that stores various setting values (parameters) required for specifying the operation of the image sensor 130 transmitted from the control unit 210. The serial access register 1306 stores setting values (parameters) related to a function of image capturing in the image sensor 130 such as, for example, an exposure time (storage time) when the image sensor 130 performs an operation of exposure (image capturing), a frame rate of a moving image, an image size (the number of pixels) indicating the size of an image to be exposed (captured), or a readout method when an imaging signal is output. In addition, the serial access register 1306 stores setting values (parameters) for controlling the operation or execution of functions other than image capturing provided in the image sensor 130 performed by each component such as, for example, the frame configuration circuit 1308 or the oscillator 1311. Here, the setting values (parameters) related to the frame configuration circuit 1308 stored by the serial access register 1306 include setting values (parameters) required for the frame configuration circuit 1308 to generate synchronizing signals (a vertical synchronizing signal and a horizontal synchronizing signal) such as, for example, a vertical blanking period (the number of horizontal synchronizing signals) or a horizontal blanking period (the number of master clock signals). In addition, the setting values (parameters) related to the oscillator 1311 stored by the serial access register 1306 include setting values (parameters) required for the oscillator 1311 to generate a reference clock signal such as, for example, an oscillation frequency (the frequency of a master clock signal).

The serial access register 1306 is a register of a serial communication scheme, and is a register capable of being controlled by the serial clock signal SCL and the serial data signal SDA synchronized therewith. That is, the serial access register 1306 is a register capable of rewriting stored setting values (parameters) through serial communication. The serial access register 1306 uses the horizontal synchronizing signal which is output from the frame configuration circuit 1308 as the serial clock signal SCL. The serial access register 1306 determines setting values (parameters) indicated by the serial data signal SDA which are transmitted from the control unit 210 on the basis of the serial clock signal SCL (the horizontal synchronizing signal), and stores the determined setting values (parameters). For example, the serial access register 1306 rewrites the currently stored setting values (parameters) to the determined setting values (parameters).

Meanwhile, the serial access register 1306 is not limited to a memory of an I2C scheme, and may be, for example, a register of a serial peripheral interface (SPI) scheme. In this case, the serial access register 1306 is configured to rewrite the stored setting values (parameters) using the horizontal synchronizing signal which is output from the frame configuration circuit 1308 as a signal equivalent to the serial clock signal SCL in an SPI scheme.

The timing generator 1307 is a timing generation circuit that generates a timing signal for controlling a timing of the entire operation in the image sensor 130. The timing generator 1307 generates a timing signal required for each component to execute a function provided in the image sensor 130 on the basis of the setting values (parameters) stored in the serial access register 1306. The timing generator 1307 outputs each generated timing signal to a corresponding component. Thereby, in the image sensor 130, each component operates at a timing according to the timing signal generated by the timing generator 1307.

Next, the configuration of the control unit 210 will be described. The control unit 210 includes a line receiver 2101, a clock data recovery (CDR) circuit 2102, an image generation unit 2103, and a register setting unit 2104.

The line receiver 2101 is a receiver circuit that receives a digital transmission signal (code differential) which is output from the image sensor 130 and is transmitted as a serial differential signal of an LVDS scheme by the differential signal line 31P and the differential signal line 31N. The line receiver 2101 converts the received digital transmission signal (code differential) from the serial differential signal of an LVDS scheme to a digital transmission signal (code) which is a single serial signal after the encoding circuit 1309 provided in the image sensor 130 performs Manchester encoding. The line receiver 2101 outputs the digital transmission signal (code) of the converted single serial signal to the clock data recovery circuit 2102.

The clock data recovery circuit 2102 is a restoration circuit that extracts (restores) a data detection clock multiplexed in synchronization with each piece of bit data from each piece of bit data constituting the digital transmission signal (code) of the single serial signal which is output from the line receiver 2101. More specifically, the clock data recovery circuit 2102 extracts the timing of a data detection clock in which the encoding circuit 1309 provided in the image sensor 130 represents the timing of switching of each piece of bit data included in the digital transmission signal with a falling edge or a rising edge. The clock data recovery circuit 2102 outputs the digital transmission signal (code) of the single serial signal which is output from the line receiver 2101 and the extracted (restored) data detection clock to the image generation unit 2103. In the control unit 210 shown in FIG. 2, the clock data recovery circuit 2102 outputs the digital transmission signal (code) of the single serial signal which is output from the line receiver 2101 as bit data Data and the extracted (restored) data detection clock as a synchronizing signal Sync to the image generation unit 2103.

Meanwhile, in the control unit 210 shown in FIG. 2, although a configuration is shown in which the digital transmission signal (code) of the single serial signal which is output from the line receiver 2101 is output to the image generation unit 2103 through the clock data recovery circuit 2102, the digital transmission signal (code) is a single serial signal as it is which is output from the line receiver 2101. Therefore, the control unit 210 may be configured such that the line receiver 2101 outputs the digital transmission signal (code) of the single serial signal to the clock data recovery circuit 2102 and the image generation unit 2103, and that the clock data recovery circuit 2102 outputs only the extracted (restored) data detection clock to the image generation unit 2103.

The image generation unit 2103 is an image processing unit that restores information indicating a synchronizing signal such as position information represented by the bit data Data output from the clock data recovery circuit 2102 or a digital imaging signal and generates a moving image captured by the image sensor 130 on the basis of the information indicating a synchronizing signal such as position information or the digital imaging signal which is restored.

The image generation unit 2103 first detects each bit data value (a data value of a "High" level or a "Low" level) included in the digital transmission signal (code) of the single serial signal on the basis of the synchronizing signal Sync which is output from the clock data recovery circuit 2102. In this case, the image generation unit 2103 detects the data value of each piece of bit data using the edge of a clock signal obtained by multiplying the synchronizing signal Sync. Thereby, the image generation unit 2103 can obtain each piece of bit data included in the digital transmission signal (code) of the single serial signal after the encoding circuit 1309 provided in the image sensor 130 performs Manchester encoding.

Thereafter, the image generation unit 2103 restores each piece of bit data included in the digital transmission signal before the encoding circuit 1309 provided in the image sensor 130 performs Manchester encoding from the detected bit data. That is, the image generation unit 2103 restores the digital transmission signal (code) of the single serial signal on which Manchester encoding is performed to the digital transmission signal of the single serial signal on which Manchester encoding is not performed.

The image generation unit 2103 converts (serial/parallel converts) the restored digital transmission signal of the single serial signal on which Manchester encoding is not performed into parallel data. Thereby, the image generation unit 2103 restores each piece of parallel data (information indicating a synchronizing signal such as position information or a digital imaging signal) included in the digital transmission signal of a moving image configured by the frame configuration circuit 1308 provided in the image sensor 130 performing the frame configuration process. That is, the image generation unit 2103 restores the synchronizing signals (the vertical synchronizing signal and the horizontal synchronizing signal) generated by the frame configuration circuit 1308 and embedded as a clock signal equivalent to the serial clock signal SCL and each digital imaging signal which is output by the column processing circuit 1304.

The image generation unit 2103 performs various types of image processing on each piece of data of the restored digital imaging signal, and generates a moving image including an observation region whose image is captured by the image sensor 130.

In addition, the image generation unit 2103 is also a synchronizing signal generation unit that generates the same synchronizing signal as the synchronizing signals (the vertical synchronizing signal and the horizontal synchronizing signal) generated by the frame configuration circuit 1308 provided in the image sensor 130 and embedded in the digital imaging signal as a clock signal equivalent to the serial clock signal SCL on the basis of the restored information indicating a synchronizing signal such as position information. That is, the image generation unit 2103 is also a synchronizing signal generation unit that generates a synchronizing signal synchronized with the synchronizing signals (the vertical synchronizing signal and the horizontal synchronizing signal) generated by the frame configuration circuit 1308. Meanwhile, in a case where a delay occurs in the transmission of the digital transmission signal (code differential) from the image sensor 130, this delay can be considered to be a fixed amount of delay. In this case, the image generation unit 2103 may be configured to generate a synchronizing signal synchronized with the synchronizing signal generated by the frame configuration circuit 1308 in consideration of the fixed amount of delay in the transmission of the digital transmission signal (code differential) from the image sensor 130.

The moving image and the synchronizing signal generated by the image generation unit 2103 are output to, for example, the color monitor 22, and a moving image captured by the image sensor 130 is displayed on the color monitor 22. In addition, the image generation unit 2103 outputs the generated synchronizing signal as the serial clock signal SCL to the register setting unit 2104 in the inside (that is, the serial access register 1306) of the image sensor 130. In the control unit 210 shown in FIG. 2, the image generation unit 2103 outputs the horizontal synchronizing signal Hsync out of the generated synchronizing signals as the serial clock signal SCL to the register setting unit 2104.

The register setting unit 2104 is a control unit that sets various setting values (parameters) for specifying the operation of the image sensor 130 in the serial access register 1306 provided in the image sensor 130. The register setting unit 2104 controls storage of the setting values (parameters) in the serial access register 1306 or rewriting of the setting values (parameters) stored in the serial access register 1306 through serial communication. In this case, the register setting unit 2104 performs serial communication with the serial access register 1306 using the horizontal synchronizing signal Hsync output from the image generation unit 2103 as the serial clock signal SCL. The register setting unit 2104 first generates a register setting signal indicating access to the serial access register 1306 when controlling storage, rewriting, or readout of the setting values (parameters) in the serial access register 1306.

For example, the register setting unit 2104 generates a register setting signal indicating the setting values (parameters) to be set in the serial access register 1306 when controlling storage or rewriting of the setting values (parameters) in the serial access register 1306. In the endoscopic device 1 using the imaging system 100, the register setting unit 2104 generates, for example, a register setting signal indicating the setting values (parameters) to be set in the image sensor 130 in order to capture an image of an observation region instructed by an inspection executor operating the operation switch 14. In addition, for example, the register setting unit 2104 generates a register setting signal for instructing the serial access register 1306 to read out the setting values (parameters) when controlling readout of the setting values (parameters) stored in the serial access register 1306. In the endoscopic device 1 using the imaging system 100, the register setting unit 2104 generates, for example, a register setting signal indicating an instruction to read out the setting values (parameters) set in the image sensor 130 in order to confirm the current setting instructed by an inspection executor operating the operation switch 14.

The register setting unit 2104 transmits the generated register setting signal as the serial data signal SDA to the image sensor 130 through the serial signal line 32 at a timing synchronized with the horizontal synchronizing signal Hsync (that is, the serial clock signal SCL).

With such a configuration, in the imaging system 100, the image sensor 130 generates a synchronizing signal, and configures a digital transmission signal for transmitting each frame (image) of a moving image in a state in which information indicating the generated synchronizing signal (such as position information) is embedded as a clock signal equivalent to the serial clock signal SCL. Thereby, in the imaging system 100, the image sensor 130 transmits the generated synchronizing signal as a clock signal equivalent to the serial clock signal SCL together with a digital imaging signal to the control unit 210. In addition, in the imaging system 100, the control unit 210 generates the same synchronizing signal as the synchronizing signal generated in the image sensor 130 on the basis of information indicating a synchronizing signal (such as position information) included in the digital transmission signal (code differential) transmitted from the image sensor 130. The imaging system 100 performs serial communication in which the generated synchronizing signal is used as the serial clock signal SCL which is used inside by the image sensor 130, and the generated serial data signal SDA is transmitted to the image sensor 130 at a timing synchronized with the serial clock signal SCL (synchronizing signal).

That is, in the imaging system 100, in general I2C serial communication, the serial clock signal SCL to be transmitted together with the serial data signal SDA from a side transmitting the serial data signal SDA is generated and transmitted at a side receiving the serial data signal SDA. In the imaging system 100, the side transmitting the serial data signal SDA transmits the generated serial data signal SDA at a timing synchronized with the serial clock signal SCL transmitted from the side receiving the serial data signal SDA.

Thereby, in the imaging system 100, it is possible to reduce a signal line for transmitting the serial clock signal SCL out of two signal lines (a signal line for the serial clock signal SCL and a signal line for the serial data signal SDA) required in the case of the general I2C serial communication between the image sensor 130 and the control unit 210. Thus, in the endoscopic device 1 using the imaging system 100, the number of signal lines in the endoscope portion 10 and the universal cord 30 is reduced by one less than in a configuration in which the general I2C serial communication is performed, thereby allowing a decrease in the diameter of the endoscope portion 10 (particularly, the insertion portion 11) to be realized.

Next, the imaging system 100 will be described in more detail. First, the digital transmission signal which is transmitted to the control unit 210 by the image sensor 130 will be described. As described above, the image sensor 130 configures a digital transmission signal in which the digital imaging signal of the captured moving image and the information indicating the generated synchronizing signal are combined, and transmits the digital transmission signal (code) of a single serial signal obtained by encoding the configured digital transmission signal to the control unit 210 using a differential serial transmission scheme of an LVDS scheme.

Figure 3:
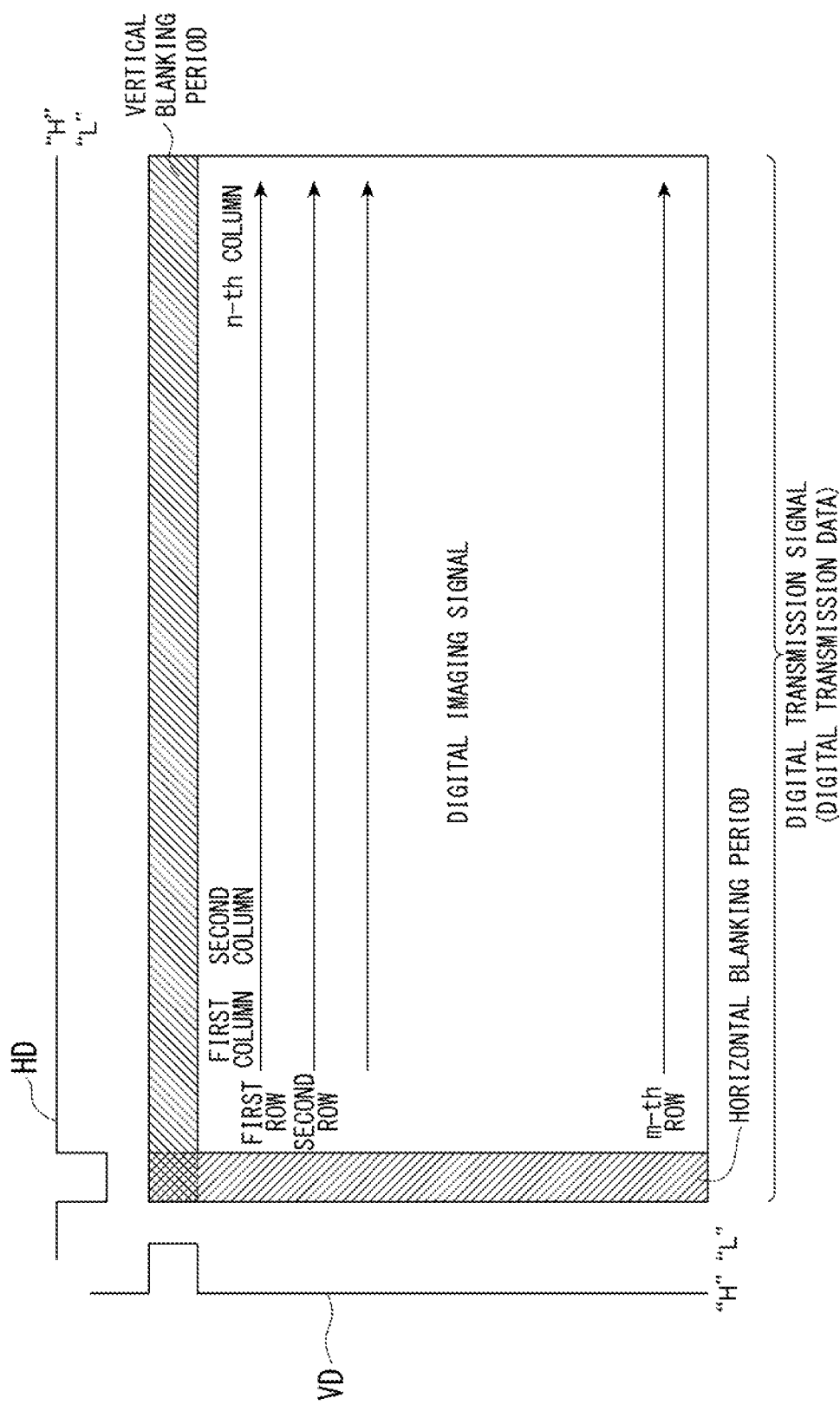
FIG. 3 is a diagram schematically illustrating a configuration of a frame of a moving image which is transmitted to a control device by a solid-state imaging device constituting the imaging system in the embodiment of the present invention.

FIG. 3 is a diagram schematically illustrating a configuration of a frame (image) of a moving image to be transmitted to a control device (the control unit 210) by a solid-state imaging device (the image sensor 130) constituting the imaging system 100 in the embodiment of the present invention. Meanwhile, in the following description, it is assumed that a digital imaging signal corresponding to each pixel in a moving image captured by the image sensor 130 is 12 bits, and that data of a digital transmission signal (hereinafter referred to as "digital transmission data") to be transmitted to the control unit 210 is 16 bits.

In the image sensor 130, the vertical scanning circuit 1303 drives each pixel disposed in the pixel unit 1302 for each row, sequentially moves the driven rows in a vertical direction (a column direction or a longitudinal direction), and outputs a pixel signal corresponding to signal charge generated by each pixel to the column processing circuit 1304. In the image sensor 130, the horizontal scanning circuit 1305 outputs a digital imaging signal which is analog/digital converted by the column processing circuit 1304 to the frame configuration circuit 1308 for each column of the pixels disposed in the pixel unit 1302. That is, in the image sensor 130, the digital imaging signal is output to the frame configuration circuit 1308 in a so-called raster order. FIG. 3 schematically shows a state in which one frame's (one image's) worth of digital imaging signals constituting a moving image is sequentially output to the frame configuration circuit 1308.

More specifically, first, the vertical scanning circuit 1303 drives pixels disposed in the first row of the pixel unit 1302 to output the pixel signal to the column processing circuit 1304, and the horizontal scanning circuit 1305 outputs a digital imaging signal corresponding to pixels disposed in the first column of the pixel unit 1302 to a digital imaging signal corresponding to pixels disposed in the n-th column in order to the frame configuration circuit 1308. Thereafter, the vertical scanning circuit 1303 drives pixels disposed in the second row of the pixel unit 1302 to output the pixel signal to the column processing circuit 1304, and the horizontal scanning circuit 1305 similarly outputs the digital imaging signals of the first column to n-th column of the pixel unit 1302 in order to the frame configuration circuit 1308. Finally, the vertical scanning circuit 1303 drives pixels disposed in the m-th row of the pixel unit 1302 to output the pixel signal to the column processing circuit 1304, and the horizontal scanning circuit 1305 outputs the digital imaging signals of the first column to n-th column of the pixel unit 1302 in order to the frame configuration circuit 1308. In the image sensor 130, one frame's (one image's) worth of digital imaging signals constituting a moving image is sequentially output to the frame configuration circuit 1308 by such operations of the vertical scanning circuit 1303 and the horizontal scanning circuit 1305. Meanwhile, the number of columns (n columns) of pixels or the number of rows (m rows) of pixels drived by the vertical scanning circuit 1303 is stored in the serial access register 1306 as the setting value (parameter) of an image size (the number of pixels) indicating the size of an image which is exposed (captured) by the image sensor 130.

Thereafter, in the image sensor 130, for every elapse of a certain period of time corresponding to the setting value (parameter) of a vertical blanking period stored in the serial access register 1306, the next one frame's (one image's) worth of digital imaging signals constituting a moving image is sequentially output to the frame configuration circuit 1308 in a raster order from the first row of the pixel unit 1302. That is, in the image sensor 130, a period in which the digital imaging signal of the frame (image) of each moving image is output to the frame configuration circuit 1308, that is, a so-called frame rate of a moving image, is determined by the setting value (parameter) of the vertical blanking period stored in the serial access register 1306.

Meanwhile, the frame rate of a moving image in which the digital imaging signal of the frame (image) of each moving image is output to the frame configuration circuit 1308 is also an image capturing period in which a moving image is captured in the image sensor 130. In capturing of a moving image in the image sensor 130, the vertical scanning circuit 1303 drives each of the pixels disposed in the pixel unit 1302 in accordance with setting values (parameters) related to a function of image capturing which is stored in the serial access register 1306. Here, as a method of driving pixels performed by the vertical scanning circuit 1303 when the image sensor 130 captures a moving image, a so-called rolling shutter-type driving in which each pixel is sequentially driven for each row or a so-called global shutter-type driving in which all pixels are simultaneously driven can be considered. However, driving of pixels performed by the vertical scanning circuit 1303 for capturing a moving image in the image sensor 130 is performed on a pixel in which output of the pixel signal of a frame (image) before a moving image is constituted is completed in a vertical blanking period or a period in which the digital imaging signal is output to the frame configuration circuit 1308 in a raster order. That is, the driving of pixels for outputting a pixel signal performed by the vertical scanning circuit 1303 and the driving of pixels for capturing a moving image are performed exclusively. In the imaging system 100, the register setting unit 2104 provided in the control unit 210 controls storage, rewriting, or readout of the setting values (parameters) in the serial access register 1306 in synchronization with a timing when the frame (image) of a moving image based on the digital imaging signal received by the control unit 210 is configured, that is, a timing when each frame (image) of a moving image captured by the image sensor 130 is displayed on the color monitor 22. Therefore, a detailed description of driving of pixels performed by the vertical scanning circuit 1303 for capturing a moving image in the image sensor 130 will not be provided below.

In addition, in the image sensor 130, the frame configuration circuit 1308 generates synchronizing signals (a vertical synchronizing signal and the horizontal synchronizing signal) corresponding to a digital imaging signal of the frame (image) of each moving image which is output by the column processing circuit 1304 on the basis of the setting values (parameters) stored in the serial access register 1306. In the image sensor 130, the frame configuration circuit 1308 configures a digital transmission signal for embedding information indicating the generated synchronizing signal (such as position information) in the digital imaging signal to transmit it to the control unit 210.

FIG. 3 shows an example of a digital transmission signal of a moving image in which information indicating each synchronizing signal of a vertical synchronizing signal VD and a horizontal synchronizing signal HD which are generated is combined with one frame's (one image's) worth of digital imaging signals constituting a moving image which is output by the column processing circuit 1304. Meanwhile, for reference, FIG. 3 shows an example of each synchronizing signal of the vertical synchronizing signal VD and the horizontal synchronizing signal HD which are generated by the frame configuration circuit 1308. In each of the vertical synchronizing signal VD and the horizontal synchronizing signal HD shown in FIG. 3, "High"="H" level indicates that the digital transmission signal is in a valid period as a moving image, and "Low"="L" level indicates that the digital transmission signal is in an invalid period as a moving image, that is, a blanking period.

The frame configuration circuit 1308 configures a digital transmission signal of a moving image in which information indicating the synchronizing signal shown in FIG. 3 and the digital imaging signal are combined. That is, the frame configuration circuit 1308 configures a digital transmission signal in which data of the same format as the digital imaging signal which is not used for the configuration of a moving image performed by the control unit 210 is embedded in the digital imaging signal output from the column processing circuit 1304 within a blanking period indicated by each of the vertical synchronizing signal VD and the horizontal synchronizing signal HD. FIG. 3 shows an example of the frame (image) of a moving image configured by embedding data which is not used for the configuration of a moving image in each of a blanking period in a vertical direction (vertical blanking period) indicated by the vertical synchronizing signal VD and a blanking period in a horizontal direction (horizontal blanking period) indicated by the horizontal synchronizing signal HD. The frame configuration circuit 1308 sequentially outputs data of information indicating each synchronizing signal included in the configured frame (image) of a moving image or the digital imaging signal to the encoding circuit 1309 for each row. In this case, the frame configuration circuit 1308 embeds the data of information indicating each synchronizing signal (position information) included in the configured frame (image) of a moving image in the data which is not used for the configuration of a moving image within each blanking period. In the image sensor 130, the encoding circuit 1309 encodes the data which is output from the frame configuration circuit 1308, that is, digital transmission data (parallel data), using the Manchester encoding scheme, and the line driver 1310 converts the encoded data into a differential signal of an LVDS scheme to transmit it to the control unit 210.

More specifically, when the digital transmission data of each row of the configured digital transmission signal is output, the frame configuration circuit 1308 sets at least all the 16 bits of the digital transmission data to be initially output to "1" (that is, "11111111_11111111"). This is because, in the image sensor 130, it is represented by the head of a row, that is, digital transmission data for outputting the start timing of the horizontal synchronizing signal HD by using the fact that the digital imaging signal corresponding to each pixel is 12 bits and that digital imaging signals represented by 16-bit digital transmission data are not all "1.". Thereby, the control unit 210 having received a digital imaging signal can recognize the head of each row in the digital transmission signal of a moving image configured by the image sensor 130, that is, the switching timing of the row by detecting digital transmission data in which all the bits are "1" from the 16-bit digital transmission data indicated by the received digital imaging signal.

Next, the frame configuration circuit 1308 represents position information in the configured digital transmission signal, that is, the position of a row, with 16-bit digital transmission data to be output next. Meanwhile, in the imaging system 100, it is determined in advance that digital transmission data next to the digital transmission data in which all the bits are "1" is data indicating the position of a row between the image sensor 130 and the control unit 210, and matching is performed therebetween. Therefore, the control unit 210 having received a digital imaging signal can recognize which row of digital imaging signal the digital transmission data indicated by a digital transmission signal to be received from 16-bit digital transmission data indicated by the digital transmission signal received next to the digital transmission data in which all the bits are "1" corresponds to.

Thereafter, the frame configuration circuit 1308 sequentially outputs the 16-bit digital transmission data indicating the digital imaging signal of each row. Here, the digital imaging signal is 12-bit data. Therefore, the frame configuration circuit 1308 allocates a digital imaging signal to, for example, low-order 12 bits out of the 16-bit digital transmission data, and outputs digital transmission data in which all the high-order 4 bits are set to "0." Thereby, the control unit 210 having received a digital imaging signal can sequentially recognize and process low-order 12 bits out of the 16-bit digital transmission data indicated by the received digital transmission signal as the digital imaging signal.

Meanwhile, in the imaging system 100, it is determined in advance how many rows' worth of periods in the digital transmission signal the vertical blanking period in the digital transmission signal of a moving image configured by the frame configuration circuit 1308 corresponds to between the image sensor 130 and the control unit 210, and matching is performed therebetween. Thereby, the control unit 210 having received a digital imaging signal recognizes in advance whether digital transmission data including a digital imaging signal constituting a moving image is received or digital transmission data in the vertical blanking period is received by receiving the digital transmission data indicating the position of a row. In addition, in the imaging system 100, it is determined in advance how long of a period in the digital transmission data the horizontal blanking period in the digital transmission signal of a moving image configured by the frame configuration circuit 1308 corresponds to between the image sensor 130 and the control unit 210, and matching is performed therebetween. Thereby, the control unit 210 having received a digital imaging signal receives digital transmission data indicating the position of a row, and then recognizes in advance the number of digital transmission data from which the digital transmission data indicating a digital imaging signal is received. Therefore, the frame configuration circuit 1308 may use any data other than the digital transmission data indicating a digital imaging signal to be output after the digital transmission data indicating the position of a row is output. Meanwhile, since the digital imaging signal is 12-bit data as described above, the frame configuration circuit 1308 may be configured such that the control unit 210 can more reliably recognize that this digital imaging signal is not digital transmission data indicating a digital imaging signal, for example, by outputting digital transmission data in which all the high-order 4 bits are set to "1."

In this manner, in the image sensor 130, when the digital transmission data of each row is output to the encoding circuit 1309, the frame configuration circuit 1308 outputs each piece of digital transmission data in the order of the digital transmission data indicating the head of a row and the digital transmission data indicating the position of a row followed by a plurality of pieces of digital transmission data indicating a digital imaging signal or a plurality of pieces of digital transmission data not indicating a digital imaging signal.

Thereafter, the frame configuration circuit 1308 completes an output of digital transmission data indicating one row of digital imaging signals or digital transmission data not indicating a digital imaging signal, and then outputs digital transmission data of the next row. In this case also, the frame configuration circuit 1308 outputs each piece of digital transmission data to the encoding circuit 1309, as described above, in order from the digital transmission data indicating the head of the next row, that is, the start timing of the horizontal synchronizing signal HD of the next row.

In the image sensor 130, the encoding circuit 1309 sequentially converts each piece of digital transmission data into a serial signal to perform Manchester encoding, and the line driver 1310 transmits a plurality of pieces of digital transmission data as digital transmission signals (code differential) to the control unit 210 through differential signals sequentially converted into an LVDS scheme. Thereby, in the control unit 210 having received the digital transmission signal (code differential), the image generation unit 2103 generates the same synchronizing signal as (the horizontal synchronizing signal Hsync in FIG. 2) the synchronizing signal generated by the frame configuration circuit 1308 provided in the image sensor 130 on the basis of a timing at which the digital transmission signal of digital transmission data indicating the head of a row is received. In the control unit 210, the register setting unit 2104 performs serial communication on the serial access register 1306 using the horizontal synchronizing signal Hsync as the serial clock signal SCL.

Meanwhile, in the imaging system 100, the control unit 210 does not transmit a master clock signal to the image sensor 130. That is, in the imaging system 100, a signal line for transmitting the master clock signal from the main body to the solid-state imaging device is also reduced in order to match the timing of operation of the solid-state imaging device provided at the distal end of the insertion portion with the timing of operation of the main body in an endoscopic device of the related art. Therefore, in the imaging system 100, the image sensor 130 is provided with the oscillator 1311. In the imaging system 100, the control unit 210 controls the frequency of the master clock signal by setting (storing) setting values (parameters) required for the oscillator 1311 to generate (oscillate) a reference clock signal (master clock signal) in the serial access register 1306. Thereby, in the imaging system 100, the period (frequency) of a synchronizing signal which is generated by the frame configuration circuit 1308 provided in the image sensor 130 is set to a constant period (frequency). In the imaging system 100, the image generation unit 2103 provided in the control unit 210 generates the same synchronizing signal as the synchronizing signal (the vertical synchronizing signal and the horizontal synchronizing signal) embedded as a clock signal equivalent to the serial clock signal SCL from the image sensor 130.

Figure 4:
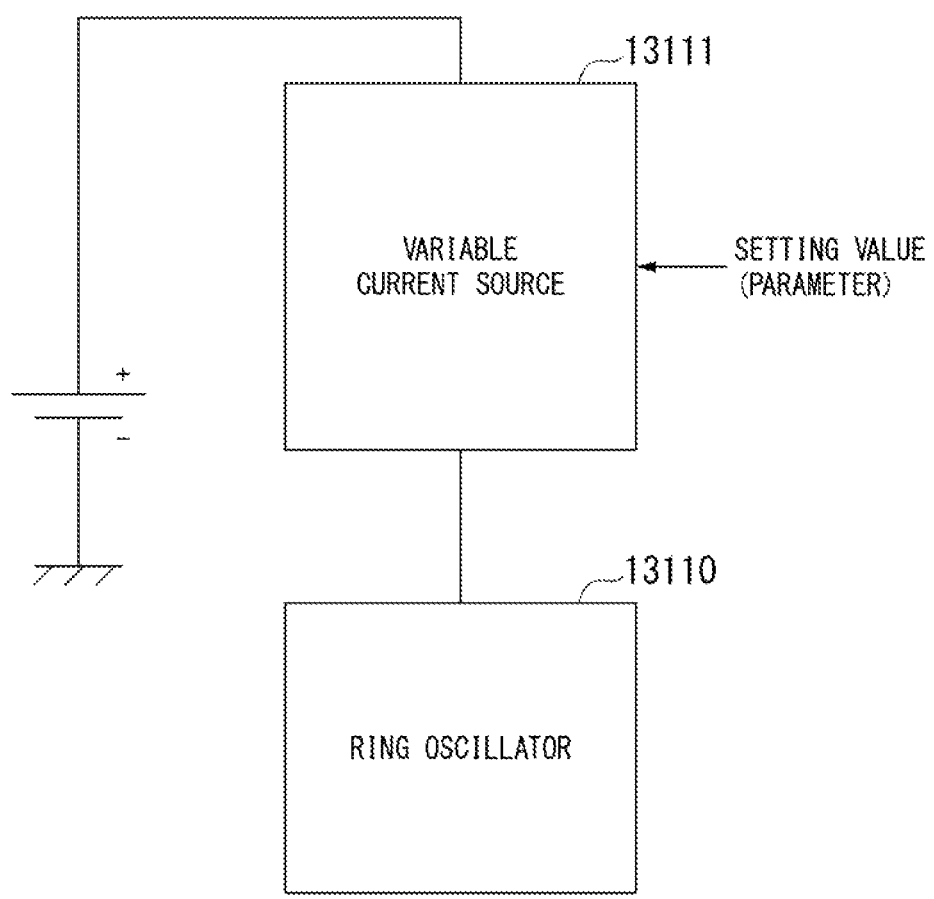
FIG. 4 is a block diagram illustrating an example of a schematic configuration of a clock oscillation circuit provided in the solid-state imaging device constituting the imaging system in the embodiment of the present invention.

Here, an example of the configuration of the oscillator 1311 provided in the image sensor 130 will be described. FIG. 4 is a block diagram illustrating an example of a schematic configuration of a clock oscillation circuit (the oscillator 1311) provided in the solid-state imaging device (the image sensor 130) constituting the imaging system 100 in the embodiment of the present invention. In FIG. 4, the oscillator 1311 is configured to include a ring oscillator 13110 and a variable current source 13111.

The ring oscillator 13110 is a clock oscillation circuit configured such that an odd number of logical negation circuits (INV circuits) are connected to each other in an annular shape. The ring oscillator 13110 oscillates a clock signal of a frequency corresponding to the value of current flowing to each INV circuit.

The variable current source 13111 is a current source that flows a current value to each INV circuit provided in the oscillator 1311. The variable current source 13111 is a digitally controlled variable current source capable of changing a current flowing in accordance with an input setting value (parameter). The setting value (parameter) of an oscillation frequency (the frequency of the master clock signal) stored in the serial access register 1306 is input to the variable current source 13111. The control unit 210 changes the frequency of a clock signal which is oscillated by the variable current source 13111 by controlling the serial access register 1306 and rewriting the setting value (parameter) of the oscillation frequency (the frequency of the master clock signal) stored in the serial access register 1306. Thereby, the control unit 210 can set the period (frequency) of the synchronizing signal generated by the frame configuration circuit 1308 provided in the image sensor 130 to a constant period (frequency).

Meanwhile, a frequency effective as the serial clock signal SCL is considered to be equal to or higher than 1 kHz and equal to or lower than 500 kHz. Therefore, the control unit 210 may set the frequency of the master clock signal which is generated by the oscillator 1311 provided in the image sensor 130 so that the frequency of a clock signal (the horizontal synchronizing signal Hsync in FIG. 2) equivalent to the serial clock signal SCL used by the register setting unit 2104 is between 1 kHz to 500 kHz. Thereby, the control unit 210 sets the period (frequency) of the synchronizing signal (more specifically, the horizontal synchronizing signal HD) generated by the frame configuration circuit 1308 to a constant period (frequency), and the image generation unit 2103 generates the same synchronizing signal as the synchronizing signal (the horizontal synchronizing signal) embedded as a clock signal equivalent to the serial clock signal SCL from the image sensor 130.

Figure 5:
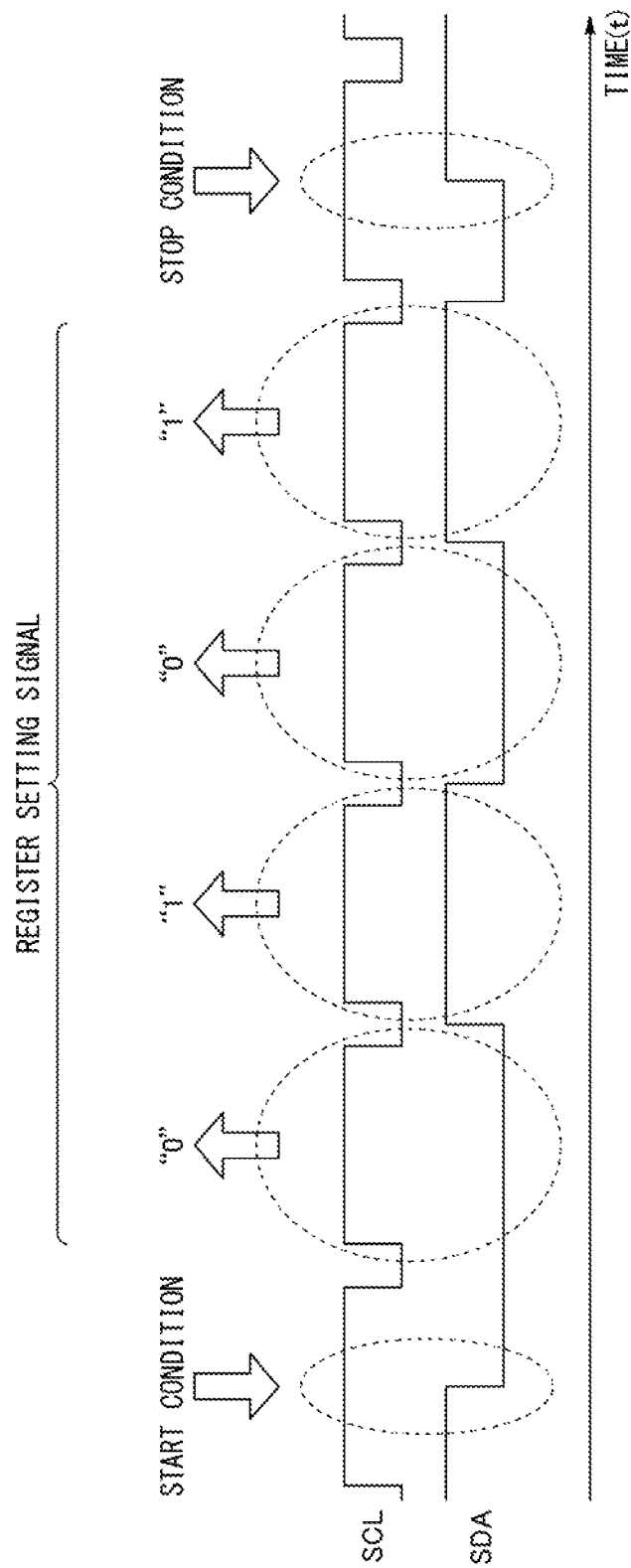
FIG. 5 is a timing chart illustrating a relationship between signals of serial communication in the imaging system in the embodiment of the present invention.

Next, the timing of serial communication performed by the control unit 210 will be described. As described above, the register setting unit 2104 provided in the control unit 210 performs serial communication on the serial access register 1306 provided in the image sensor 130 using the synchronizing signal (the horizontal synchronizing signal Hsync in FIG. 2) which is output from the image generation unit 2103 as the serial clock signal SCL. FIG. 5 is a timing chart illustrating a relationship between signals of serial communication in the imaging system 100 in the embodiment of the present invention. FIG. 5 shows an example of the timing of the horizontal synchronizing signal Hsync as the serial clock signal SCL. In addition, FIG. 5 shows an example of the timing of a register setting signal which is output by the register setting unit 2104 as the serial data signal SDA.

The timing of serial communication in the imaging system 100 is the same as the timing of the general I2C serial communication. More specifically, the register setting unit 2104 sets a start condition by setting the serial data signal SDA to a "Low" level (that is, providing a falling edge) during a period in which the serial clock signal SCL is at a "High" level. In addition, the register setting unit 2104 sets a stop condition by setting the serial data signal SDA to a "High" level (that is, providing a rising edge) during a period in which the serial clock signal SCL is at a "High" level. In addition, in a period between the start condition and the stop condition, the register setting unit 2104 transmits data by switching the level of the serial data signal SDA to the level of data to be transmitted when the serial clock signal SCL is at a "Low" level and maintaining the level of the serial data signal SDA during a period in which the serial clock signal SCL is at a "High" level. FIG. 5 shows a timing in a case where the register setting unit 2104 transmits data of "0101" as data of the register setting signal to the serial access register 1306.

Meanwhile, an example of the timing of serial communication shown in FIG. 5 shows a case where the same horizontal synchronizing signal Hsync as the horizontal synchronizing signal HD shown in FIG. 3 which is generated by the frame configuration circuit 1308 provided in the image sensor 130 is used as the serial clock signal SCL as it is. That is, a case where the period of a "High" level and the period of a "Low" level in the serial clock signal SCL are different from each other, that is, a so-called duty ratio is non-uniform is shown. Incidentally, in the serial communication, as described above, the level of the serial data signal SDA is switched to the level of data to be transmitted when the serial clock signal SCL is at a "Low" level. Therefore, in the serial communication, when the period in which the serial clock signal SCL is at a "Low" level is made longer than in an example of the timing shown in FIG. 5, a margin occurs in the operation timing of the register setting unit 2104. For example, when the duty ratio of the serial clock signal SCL is 50%, a margin occurs in the operation timing of the register setting unit 2104 more than in an example of the timing shown in FIG. 5.

Moreover, in the imaging system 100, in a case where the timing of the head of each row, that is, the timing of start of the horizontal synchronizing signal HD is known from digital transmission data which is transmitted to the control unit 210 by the image sensor 130, the image generation unit 2103 can generate the horizontal synchronizing signal Hsync. In the imaging system 100, a timing at which a digital transmission signal effective as a moving image is transmitted can be specified by the setting values (parameters) of the serial access register 1306 or the like.

Therefore, in the imaging system 100, the duty ratios of the serial clock signal SCL are determined in advance and matched between the image sensor 130 and the control unit 210. That is, in the imaging system 100, duty ratios of the horizontal synchronizing signal which is generated by the frame configuration circuit 1308 provided in the image sensor 130 and is used as the serial clock signal SCL by the serial access register 1306 and the horizontal synchronizing signal Hsync which is generated by the image generation unit 2103 provided in the control unit 210 and is used as the serial clock signal SCL by the register setting unit 2104 are matched in advance. Thereby, in the imaging system 100, the serial clock signal SCL (for example, the serial clock signal SCL having a duty ratio of 50%) having a duty ratio different from the horizontal synchronizing signal HD shown in FIG. 3 or the horizontal synchronizing signal Hsync shown in FIG. 5 can be used for serial communication. That is, in the imaging system 100, in a case where the duty ratio in each serial clock signal SCL of the serial clock signal SCL used by the serial access register 1306 provided in the image sensor 130 and the serial clock signal SCL used by the register setting unit 2104 provided in the control unit 210 is shared, the serial clock signal SCL of any duty ratio can be used for serial communication.

Meanwhile, in an example of the timing of serial communication shown in FIG. 5, the start condition and the stop condition are specified when the serial clock signal SCL is at a "High" level, and an example of a timing at which the level of the serial data signal SDA during a period in which the serial clock signal SCL is at a "High" level is transmitted as data is shown. However, in serial communication in the imaging system 100, in a case where the switching timing of the serial clock signal SCL is known, the "High" level and the "Low" level of the serial clock signal SCL may be reversed. Further, in the imaging system 100, in a case where a switching timing between the serial clock signal SCL used by the serial access register 1306 provided in the image sensor 130 and the serial clock signal SCL used by the register setting unit 2104 provided in the control unit 210 is synchronized, the "High" level and the "Low" level in each of the serial clock signals SCL may be different from each other.

Meanwhile, in the imaging system 100, it is possible to perform serial communication for the control unit 210 to read out the setting values (parameters) stored in the serial access register 1306. In this case, in the imaging system 100, the register setting unit 2104 instructs the serial access register 1306 to perform readout through serial communication, and the serial access register 1306 outputs a signal indicating the stored setting value (parameter) as the serial data signal SDA to the serial signal line 32. That is, in the imaging system 100, it is possible to perform bidirectional serial communication between the image sensor 130 and the control unit 210. Therefore, the serial signal line 32 has a so-called open drain configuration in which it is connected to a power supply and pulled up by a resistor (not shown) having a predetermined resistance value. However, in the imaging system 100, in a case where the control unit 210 does not read out the setting value (parameter) stored in the serial access register 1306, the serial signal line 32 does not have to have an open drain configuration. In this case, the serial access register 1306 provided in the image sensor 130 may also not have a configuration in which the setting value (parameter) stored in response to a readout instruction is transmitted, and the circuit scale of the serial access register 1306 can be reduced. In addition, since an open drain scheme is generally unsuitable for coping with long-distance transmission, avoiding an open drain scheme in a connection configuration with serial communication oriented toward write-only without readout is advantageous for application to long cables such as endoscopic devices.

According to the embodiment, there is provided an imaging system (an imaging system 100) including: a solid-state imaging device (an image sensor 130) configured to have a plurality of pixels disposed in a two-dimensional matrix and to transmit an imaging signal (a digital imaging signal) of a captured consecutive image (a moving image), the solid-state imaging device being provided in an insertion portion (an insertion portion 11) to be inserted into a body of a patient (a subject to be inspected) in an endoscopic device (an endoscopic device 1); and a control device (a control unit 210) configured to process the digital imaging signal transmitted from the image sensor 130 and to control an operation of the image sensor 130, the control device being provided in an external processing portion (an external processing portion 21) not to be inserted into the body of the subject to be inspected in the endoscopic device 1, wherein the image sensor 130 includes a pixel unit (a pixel unit 1302) that acquires the imaging signal (a pixel signal), a register (a serial access register 1306) that stores setting values (parameters) for specifying the operation of the image sensor 130, a processing circuit (a column processing circuit 1304) that converts the pixel signal into a digital imaging signal through analog/digital conversion, a frame configuration unit (a frame configuration circuit 1308) that generates a serial digital transmission signal in which a synchronizing signal (that may be a horizontal synchronizing signal HD or a vertical synchronizing signal VD) synchronized with a horizontal synchronizing signal (a horizontal synchronizing signal HD) of the captured image (the moving image) is embedded in the digital imaging signal as a first serial clock signal (a serial clock signal SCL), and a data transmission unit (that may include a line driver 1310 or an encoding circuit 1309) that transmits data of the digital transmission signal, the control unit 210 includes a clock generation unit (an image generation unit 2103) that generates a second serial clock signal (a horizontal synchronizing signal Hsync) synchronized with the serial clock signal SCL (the horizontal synchronizing signal HD) embedded in the digital imaging signal included in the transmitted digital transmission signal, and a register setting unit (a register setting unit 2104) that transmits a register setting signal for performing control on the serial access register 1306 in synchronization with the horizontal synchronizing signal Hsync, and the serial access register 1306 determines control indicated by the transmitted register setting signal using the serial clock signal SCL and stores the setting values (parameters) in accordance with a determination result.

In addition, according to the embodiment, the imaging system 100 is configured in which the serial clock signal SCL is a horizontal synchronizing signal (a horizontal synchronizing signal HD) corresponding to the image (the moving image).

In addition, according to the embodiment, the imaging system 100 is configured in which a frequency of the serial clock signal SCL is equal to or higher than 1 kHz and equal to or lower than 500 kHz.

In addition, according to the embodiment, the imaging system 100 is configured in which the line driver 1310 transmits data of the digital transmission signal with two differential signals (for example, differential signals of an LVDS scheme), and the register setting unit 2104 transmits the register setting signal with one single signal (for example, a serial data signal SDA in I2C serial communication).

In addition, according to the embodiment, the imaging system 100 is configured in which the register setting unit 2104 only transmits the register setting signal, and does not receive a signal (in other words, does not read out the setting values (parameters) stored in the serial access register 1306).

In addition, according to the embodiment, the imaging system 100 is configured in which the image sensor 130 further includes a clock oscillation circuit (a oscillator 1311) that oscillates and outputs a reference clock signal (a master clock signal), the register setting unit 2104 stores a setting signal (setting value (parameter)) of an oscillation frequency of master clock signal in the serial access register 1306, and the oscillator 1311 oscillates the master clock signal of a frequency according to the setting signal (setting value (parameter)) of the oscillation frequency of the master clock signal stored in the serial access register 1306.

In addition, according to the embodiment, there is provided an endoscopic device (an endoscopic device 1) (using the imaging system 100) configured to include the imaging system 100, wherein the image sensor 130 is disposed at a distal end (an imaging portion 13) of an insertion portion (an insertion portion 11), and the control unit 210 is disposed in a main body (a main body 20 or an external processing portion 21 configured in the main body 20).

As described above, according to the embodiment of the present invention, the solid-state imaging device constituting the imaging system used as the endoscopic device generates a synchronizing signal (a vertical synchronizing signal and a horizontal synchronizing signal) corresponding to a frame (image) constituting the captured moving image, configures a digital transmission signal of a moving image in which information indicating the generated synchronizing signal is embedded in the digital imaging signal of the moving image, and transmits to the control device constituting the imaging system. That is, in the embodiment of the present invention, the solid-state imaging device transmits the digital transmission signal of a moving image with the start timing of the synchronizing signal in the captured moving image embedded to the control device. In the embodiment of the present invention, the control device generates the same synchronizing signal as the synchronizing signal generated by the solid-state imaging device on the basis of the information indicating the synchronizing signal embedded in the transmitted digital transmission signal of a moving image, that is, the start timing of the synchronizing signal, and generates a moving image based on the digital imaging signal included in the transmitted digital transmission signal of a moving image.

In addition, in the embodiment of the present invention, the control device constituting the imaging system performs serial communication with the solid-state imaging device when controlling the operation or execution of a function of each component provided in the solid-state imaging device. In this case, in the embodiment of the present invention, the register setting unit provided in the control device transmits the serial data signal SDA using the same synchronizing signal as that of the solid-state imaging device generated in the control device as a clock signal equivalent to the serial clock signal SCL, and rewrites the setting values (parameters) stored in the serial access register provided in the solid-state imaging device. In the embodiment of the present invention, the serial access register receives the setting values (parameters) indicated by the serial data signal SDA transmitted from the control device using the synchronizing signal generated in the solid-state imaging device as the serial clock signal SCL, and rewrites the stored setting values (parameters). That is, in the embodiment of the present invention, each of the solid-state imaging device and the control device constituting the imaging system generates the synchronized serial clock signal SCL and performs serial communication. Thereby, in the embodiment of the present invention, it is possible to reduce a signal line for transmitting the serial clock signal SCL out of two signal lines of the serial clock signal SCL and the serial data signal SDA for performing serial communication between the solid-state imaging device and the control device constituting the imaging system.

Thereby, in the embodiment of the present invention, in the endoscopic device using the imaging system, the number of signal lines in the endoscope portion and the electrical signal cable is reduced by one less than the endoscopic device having a configuration in which the general I2C serial communication is performed, thereby allowing a decrease in the diameter of the endoscope portion (particularly, the insertion portion) to be realized. In addition, in the embodiment of the present invention, the number of signal lines used for serial communication is reduced, and thus the number of pads formed in the solid-state imaging device constituting the imaging system is reduced. Thereby, in the embodiment of the present invention, the area (projection area) of the solid-state imaging device constituting the imaging system is reduced, and the mounting area of the solid-state imaging device, thereby allowing a decrease in the size of the endoscope portion (particularly, the imaging portion provided at the distal end of the insertion portion) to be realized.

Meanwhile, in the embodiment of the present invention, in the imaging system (the imaging system 100 in the embodiment) of the present invention, a configuration in which the horizontal synchronizing signal (the horizontal synchronizing signal HD or the horizontal synchronizing signal Hsync in the embodiment) is used as a clock signal equivalent to the serial clock signal SCL has been described. However, in the imaging system of the present invention, the signal used as a clock signal equivalent to the serial clock signal SCL is not limited to the horizontal synchronizing signal shown in the embodiment of the present invention. That is, in the imaging system of the present invention, insofar as the signal used as a clock signal equivalent to the serial clock signal SCL is a clock signal which is generated in the image sensor 130, embedded in the digital imaging signal, and transmitted to the control unit 210 as a digital transmission signal, any clock signal may be used. However, in the imaging system of the present invention, in order for the clock data recovery circuit 2102 to restore each piece of data (bit data) included in the digital transmission signal (code) received by the control unit 210, the data detection clock multiplexed by the encoding circuit 1309 in the Manchester encoding scheme or the 8b/10b encoding scheme is not used as a clock signal equivalent to the serial clock signal SCL. In addition, in the imaging system of the present invention, the master clock signal generated by the oscillator 1311 as a reference clock signal in the image sensor 130 is also not used as a clock signal equivalent to the serial clock signal SCL. In addition, in the imaging system of the present invention, a signal indicating a timing at which the vertical scanning circuit 1303 outputs a pixel signal from the pixel unit 1302 or a signal of a timing at which the horizontal scanning circuit 1305 outputs a digital imaging signal from the column processing circuit 1304, that is, a timing of the digital imaging signal included in the digital transmission signal configured by the frame configuration circuit 1308 is also not used as a clock signal equivalent to the serial clock signal SCL. This is because a signal of a period (frequency) indicating the timing of the data detection clock, the master clock signal, or the digital imaging signal is a signal having a shorter period (a higher frequency) than a signal of a period (frequency) equal to or higher than 1 kHz and equal to or lower than 500 kHz considered to be a frequency effective as the serial clock signal SCL described above.

Therefore, in the imaging system of the present invention, for example, a vertical synchronizing signal can be considered as a signal used as a clock signal equivalent to the serial clock signal SCL instead of the horizontal synchronizing signal. That is, the imaging system 100 may be configured such that the vertical synchronizing signal which is generated by the frame configuration circuit 1308 is used as a clock signal equivalent to the serial clock signal SCL. In this case, in the imaging system 100, the image generation unit 2103 outputs the generated vertical synchronizing signal to the register setting unit 2104, and the register setting unit 2104 uses the vertical synchronizing signal which is output from the image generation unit 2103 as the serial clock signal SCL to perform serial communication on the serial access register 1306. However, the vertical synchronizing signal is a signal matching a period (frequency) equal to or higher than 1 kHz and equal to or lower than 500 kHz considered to be a frequency effective as the serial clock signal SCL described above, but is a signal having a longer period (a lower frequency) than the horizontal synchronizing signal shown in the embodiment. Therefore, in a case where the vertical synchronizing signal is used as a clock signal equivalent to the serial clock signal SCL in the imaging system 100, it can be considered that serial communication for the serial access register 1306, that is, rewriting of the setting values (parameters) stored in the serial access register 1306 is delayed more than in a case where the horizontal synchronizing signal is used as a clock signal equivalent to the serial clock signal SCL. However, in a case where the speed of rewriting of the setting values (parameters) stored in the serial access register 1306 is not an important item in the imaging system 100, or the like, the vertical synchronizing signal can be used as a clock signal equivalent to the serial clock signal SCL without any problem. Meanwhile, the operation of the imaging system 100 in this case can be considered to be similar to the operation in which the above-described horizontal synchronizing signal is used as the serial clock signal SCL, and thus a detailed description thereof will not be provided.

In addition in the embodiment of the present invention, in the imaging system 100, a description has been provided of a configuration in which the horizontal synchronizing signal Hsync is generated by the image generation unit 2103 from data of the digital transmission signal (digital transmission data) transmitted to the control unit 210 by the image sensor 130 on the basis of the timing of the head of each row, that is, the start timing of the horizontal synchronizing signal HD, and is used as the serial clock signal SCL. However, in the imaging system of the present invention, a timing serving as a reference when the serial clock signal SCL used in serial communication is generated is not limited to the start timing of the horizontal synchronizing signal HD shown in the embodiment of the present invention. That is, in the imaging system 100, in a case where a timing serving as a reference when the serial clock signal SCL is generated between the image sensor 130 and the control unit 210 is matched in advance, a position other than the head in each row such as, for example, a timing at which a blanking period ends in the horizontal synchronizing signal HD may be used as a timing serving as a reference when the serial clock signal SCL is generated. Meanwhile, the operation of the imaging system 100 in this case can be considered to be similar to the operation in which the above-described horizontal synchronizing signal is used as the serial clock signal SCL, and thus a detailed description thereof will not be provided.

Meanwhile, in the embodiment of the present invention, in the imaging system 100, a configuration in which the frame configuration circuit 1308 generates the synchronizing signal (the vertical synchronizing signal VD and the horizontal synchronizing signal HD) corresponding to each frame (image) constituting a moving image has been described. However, a component that generates the synchronizing signal in the imaging system of the present invention is not limited to the frame configuration circuit 1308 in the embodiment of the present invention. That is, in the imaging system 100, the frame configuration circuit 1308 is only required to be at least a component that configures a digital transmission signal of a moving image in which information indicating a synchronizing signal is embedded in a digital imaging signal, and the synchronizing signal may be generated by another component such as, for example, the timing generator 1307.

Meanwhile, in the embodiment of the present invention, a case in which the imaging system of the present invention is used as the endoscopic device of the present invention has been described. However, a device in which the imaging system of the present invention is used is not limited to the endoscopic device shown in the embodiment, and the idea of the imaging system of the present invention can be applied to various devices insofar as it is a device that transmits data through serial communication. The same effect can be obtained in various devices to which the idea of the imaging system of the present invention is applied.

Hereinbefore, although preferred embodiments of the present invention have been described, the present invention is not limited to the embodiments and modification examples. Additions, omissions, substitutions, and other changes of components can be made without departing from the spirit or scope of the present invention.

In addition, the present invention is not limited by the above description, and is limited only by the appended claims.

What is claimed is:

1. An imaging system comprising:
a solid-state imaging device in which a plurality of pixels are arranged in a two-dimensional matrix, and configured to transmit an imaging signal of a continuous image that has been captured; and
a control device configured to process the imaging signal transmitted from the solid-state imaging device, and to control an operation of the solid-state imaging device, wherein the solid-state imaging device includes:
a clock oscillation circuit configured to oscillate and output a reference clock signal;
a pixel unit configured to acquire the imaging signal;
a register configured to store a setting value that defines the operation of the solid-state imaging device;
a processing circuit configured to convert the imaging signal into a digital imaging signal by performing an analog/digital conversion;
a frame configuration circuit configured to generate a serial digital transmission signal that is acquired by embedding a first serial clock signal in the digital imaging signal, wherein the first serial clock signal is a synchronizing signal synchronized with a horizontal synchronizing signal of the captured image; and
a data transmission unit configured to transmit data of the digital transmission signal,
the control device includes:
a clock generation unit configured to generate a second serial clock signal synchronized with the first serial clock signal embedded in the digital imaging signal included in the digital transmission signal that has been transmitted; and
a register setting unit configured to transmit a register setting signal that controls the register in synchronization with the second serial clock signal,
the frame configuration circuit outputs the generated first serial clock signal to the register,
the register determines a control represented by the transmitted register setting signal using the first serial clock signal output from the frame configuration circuit, and stores the setting value according to a determination result, and
the reference clock signal has a higher frequency than the first serial clock signal,
wherein the first serial clock signal, which is embedded in the digital imaging signal and transmitted to the control device, is the same horizontal synchronizing signal used for operation of capturing the image.

2. The imaging system according to claim 1, wherein the first serial clock signal is a horizontal synchronizing signal corresponding to the image.

3. The imaging system according to claim 1, wherein a frequency of the first serial clock signal is 1 kHz or more and 500 kHz or less.

4. The imaging system according to claim 1, wherein
the data transmission unit transmits data of the digital transmission signal by two differential signals, and
the register setting unit transmits the register setting signal by a single signal.

5. The imaging system according to claim 1, wherein the register setting unit only transmits the register setting signal, and not performs a reception of a signal.

6. The imaging system according to claim 1, wherein
the register setting unit makes the register store a setting signal of a oscillation frequency of the reference clock signal, and
the clock oscillator circuit oscillates the reference clock signal having a frequency according to the setting signal with the oscillation frequency stored in the register.

7. An endoscopic device comprising the imaging system according to claim 1, wherein
the solid-state imaging device is arranged at a distal end of an insertion portion, and
the control device is arranged in a main body.

* * * * *